(12) United States Patent
Meshram et al.

(10) Patent No.: US 10,650,844 B2
(45) Date of Patent: May 12, 2020

(54) METHOD AND RESPONSE RECOMMENDATION SYSTEM FOR RECOMMENDING A RESPONSE FOR A VOICE-BASED USER INPUT

(71) Applicant: WIPRO LIMITED, Bangalore (IN)

(72) Inventors: Amol Meshram, Nagpur (IN); Vikash Kumar, Patna (IN); Adlla Raju, Hyderabad (IN)

(73) Assignee: Wipro Limited, Bangalore (IN)

(*) Notice: Subject to any disclaimer, the term of this patent is extended or adjusted under 35 U.S.C. 154(b) by 179 days.

(21) Appl. No.: 15/911,579

(22) Filed: Mar. 5, 2018

(65) Prior Publication Data

US 2019/0221228 A1 Jul. 18, 2019

(30) Foreign Application Priority Data

Jan. 18, 2018 (IN) .............................. 201841002124

(51) Int. Cl.
*G10L 21/00* (2013.01)
*G10L 25/66* (2013.01)
*G10L 15/02* (2006.01)
*G10L 15/22* (2006.01)
(Continued)

(52) U.S. Cl.
CPC ............ *G10L 25/66* (2013.01); *A61B 5/4803* (2013.01); *G10L 15/02* (2013.01); *G10L 15/22* (2013.01); *G16H 50/20* (2018.01); *G10L 2015/223* (2013.01); *G10L 2015/227* (2013.01)

(58) Field of Classification Search
None
See application file for complete search history.

(56) References Cited

U.S. PATENT DOCUMENTS

| | | | | |
|---|---|---|---|---|
| 7,529,670 B1 * | 5/2009 | Michaelis | .............. | A61B 5/091 381/84 |
| 8,914,286 B1 * | 12/2014 | Secker-Walker | ....... | G10L 15/00 704/231 |
| 9,093,061 B1 * | 7/2015 | Secker-Walker | ....... | G10L 15/00 |

(Continued)

FOREIGN PATENT DOCUMENTS

| | | |
|---|---|---|
| JP | 2010-197859 | 9/2010 |
| WO | WO 2015/090215 | 6/2015 |

(Continued)

*Primary Examiner* — Satwant K Singh
(74) *Attorney, Agent, or Firm* — Finnegan, Henderson, Farabow, Garrett & Dunner, LLP

(57) ABSTRACT

Disclosed herein is a method and system for recommending a response for a voice-based user input. The method includes detecting voice-based user input or input based on a query provided by a user. The method includes, extracting one or more voice parameters from pronunciation of the input. Thereafter, a disease type associated with the user is identified based on one or more voice parameters. Further, system verifies correctness of each word in the input based on comparison of each of the one or more voice parameters with a first set of predetermined corresponding one or more voice parameters associated with the disease type. Finally, the response is recommended for the input based on verification of correctness of each word in the input. The present disclosure recommends an accurate response for the input since one or more words detected incorrectly are auto corrected and provides a better user experience.

18 Claims, 4 Drawing Sheets

(51) Int. Cl.
*G16H 50/20* (2018.01)
*A61B 5/00* (2006.01)

(56) References Cited

U.S. PATENT DOCUMENTS

| | | | |
|---|---|---|---|
| 9,734,819 B2* | 8/2017 | Gray | G10L 15/30 |
| 10,290,300 B2* | 5/2019 | Pashine | G10L 15/02 |
| 10,388,272 B1* | 8/2019 | Thomson | G10L 15/063 |
| 10,431,203 B2* | 10/2019 | Millen | G06F 40/216 |
| 2008/0147404 A1 | 6/2008 | Liu et al. | |
| 2016/0293159 A1 | 10/2016 | Belisario et al. | |
| 2016/0379626 A1 | 12/2016 | Deisher et al. | |
| 2017/0017642 A1* | 1/2017 | Cunningham | G06F 17/289 |
| 2017/0148432 A1 | 5/2017 | Jaramillo et al. | |
| 2017/0169814 A1* | 6/2017 | Pashine | G10L 15/22 |
| 2018/0068031 A1* | 3/2018 | Hewavitharana | G06N 20/00 |
| 2018/0268818 A1* | 9/2018 | Schoenmackers | G10L 15/1815 |
| 2019/0012714 A1* | 1/2019 | Bright | G06Q 30/0617 |

FOREIGN PATENT DOCUMENTS

| | | |
|---|---|---|
| WO | WO 2016/014970 | 1/2016 |
| WO | WO 2017/015220 | 1/2017 |

\* cited by examiner

METHOD AND RESPONSE RECOMMENDATION SYSTEM FOR RECOMMENDING A RESPONSE FOR A VOICE-BASED USER INPUT

TECHNICAL FIELD

The present subject matter is generally related to artificial intelligence based human-machine interaction systems and more particularly, but not exclusively, to a method and system for recommending a response for a voice-based user input.

BACKGROUND

With advancement in computer technology, handheld devices have been integrated with voice based intelligent systems [alternatively referred as system] to help users in performing different tasks or operations such as scheduling appointments, booking movie tickets, online shopping and the like.

Generally, speech parameters of every individual are different. Therefore, words uttered by every user while performing such tasks or operations may differ largely due to the impact of corresponding mother tongue influence and state of user. The ambiguity in pronunciation of words is due to vocal chords, region influence and medical profile of the user. In such situations, if the user provides an input to the system, the system may misinterpret the words spoken as some other words. Thus, resulting in a reduced user experience and the action performed by the system or the response provided by the system for the user input may not be efficient. As an example, consider a scenario where the user provides a query to the system. The query may be:
Query: "Can you book me a ticket to kodaikanal"?

The system may misinterpret the word "Kodaikanal" as some other name and hence recommends a response or provides options which are out of context to the user. Because of this, the user may have to continuously provide the query unless the system detects all the words correctly. This may lead to a wastage of time and a reduced user experience.

The existing methods address the above-mentioned problems through methods such as speech recognition method, speech to text conversion method, regional based accent neutralization and the like. In the speech recognition method, the speech parameters are extracted based on which the response is provided to the user. But the method fails to correctly interpret words uttered by the user based on the speech parameters. In the speech to text conversion method, the system fails to convert similarly placed words and interpret words incorrectly. Thus, attempting to recognize words by converting speech into text predicts more words and due to more number of words the system may misinterpret the words uttered by the user. In the regional based accent neutralization, based on influence of mother tongue, the system would correct the word. But the system may not consider parameters which affects the pronunciation of words being uttered by the user when providing the query and thereby affecting the response being provided by the system.

SUMMARY

Disclosed herein is a method of recommending a response for a voice-based user input. The method comprises detecting, by a response recommendation system, the voice-based user input, wherein the voice-based user input corresponds to a query provided by a user. The method extracts one or more voice parameters from pronunciation of the voice-based user input. Based on the one or more voice parameters, a disease type associated with the user is identified. Further, the method comprises verifying correctness of each word in the voice-based user input based on comparison of each of the one or more voice parameters with a first set of predetermined corresponding one or more voice parameters associated with the disease type. Once the correctness is verified, the method recommends the response for the voice-based user input.

Further, the present disclosure relates to a system for recommending a voice-based user input. The system comprises a processor and a memory. The memory is communicatively coupled to the processor, wherein the memory stores the processor-executable instructions, which, on execution, causes the processor to detect the voice-based user input, wherein the voice-based user input corresponds to a query provided by a user. Further, the processor extracts one or more voice parameters from pronunciation of the voice-based user input. Thereafter, the processor identifies a disease type associated with the user based on the one or more voice parameters and verifies correctness of each word in the voice-based user input. The correctness is verified based on comparison of each of the one or more voice parameters with a first set of predetermined corresponding one or more voice parameters associated with the disease type. The system recommends the response for the voice-based user input based on verification of the correctness of each word in the voice-based user input.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and regarding the accompanying figures, in which:

Figure 1:
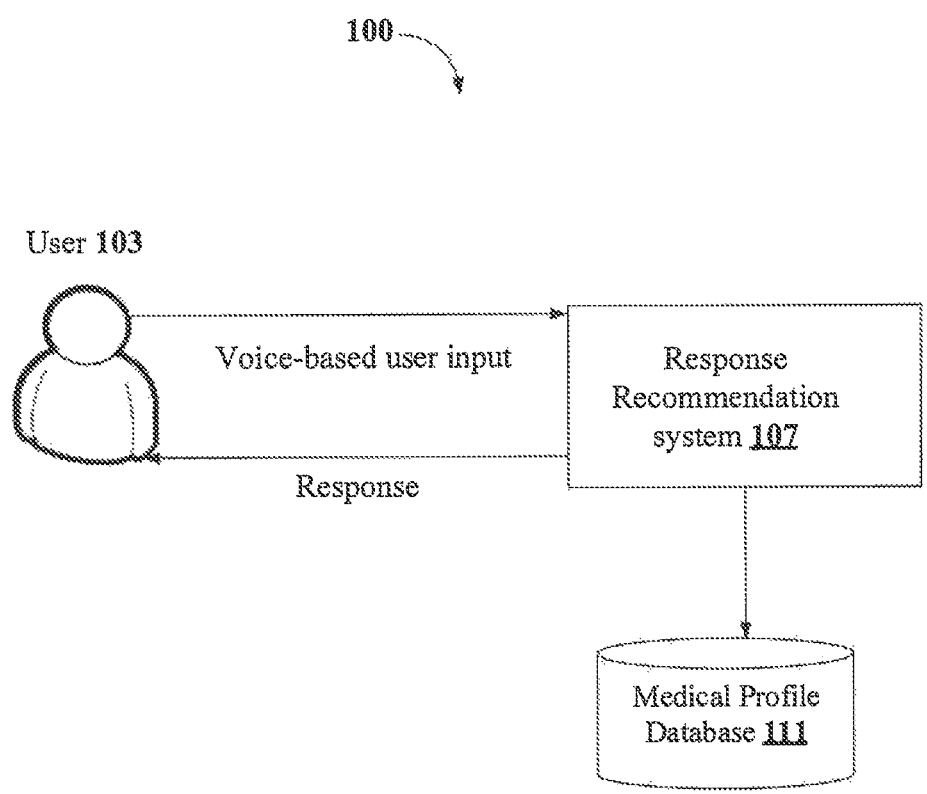
FIG. 1 illustrates an exemplary environment for recommending a response for a voice-based user input in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the specific forms disclosed, but on the contrary, the disclosure is to cover all modifications, equivalents, and alternative falling within the spirit and the scope of the disclosure.

The terms "comprises", "comprising", "includes", "including" or any other variations thereof, are intended to cover a non-exclusive inclusion, such that a setup, device, or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The present disclosure relates to a method and a system for recommending a response for a voice-based user input. The system detects the voice-based user input corresponding to a query provided by a user. Once the voice-based user input is detected, the system extracts one or more voice parameters from pronunciation of the voice-based user input. The one or more voice parameters may include at least one of pitch range, word spacing [in terms of time gap between words], frequency, speed at which each word is uttered, phonation threshold pressure and time taken to utter the voice-based user input and any other parameter which serves the purpose. Based on the extracted one or more voice parameters, the system identifies a disease type associated with the user. The system then compares each of the one or more voice parameters with a first set of predetermined corresponding one or more voice parameters to verify correctness of each word in the voice-based user input. The first set of predetermined corresponding one or more voice parameters corresponds to the disease type identified by the system. The correctness is verified by comparing each word in the voice-based input with each word in a voice based input uttered by one or more users during normal condition. Based on the comparison, the system identifies one or more words which are detected incorrectly. Thereafter, the system performs auto-correction of the one or more words which are detected incorrectly and forms a corrected voice-based user input.

Further, the corrected voice-based user input is validated using a neural network technique. As an example, Long Short Term Memory [LSTM] model may be used to validate the corrected voice-based user input. Once the corrected voice-based user input is validated, the system provides the response for the validated corrected voice-based user input.

In some embodiment of the disclosure, the system automatically corrects one or more words which are detected incorrectly in the voice-based user input prior to providing the response. Hence, the present disclosure provides a better user experience and reduced time in providing response to the user as the user may not provide the same query repeatedly to receive the corrected voice-based user input. Also, in the present disclosure, the correction of the one or more words is performed by considering medical profile, state of the user, and context in which the user is uttering the word and hence provides an accurate recommendation of the response.

In the following detailed description of the embodiments of the disclosure, reference is made to the accompanying drawings that form a part hereof, and in which are shown by way of illustration of embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an exemplary environment for recommending a response for a voice-based user input in accordance with some embodiments of the present disclosure.

The environment 100 includes a user 103, a response recommendation system 107 and a medical profile database 111. The user 103 may provide a voice-based user input [alternatively referred as input] to the response recommendation system 107 [alternatively referred as system 107]. The voice-based user input corresponds to a query provided by the user 103. In order to provide the response for the voice-based user input, the system 107, before providing the response to the input, has to detect or interpret the input correctly. If the system 107 detects the input correctly then the system 107 may recommend the response which corresponds to the input. In another scenario, the system 107 may detect the input incorrectly, in such scenarios, there is a need for the system 107 to automatically correct the input and then recommend the response.

As an example, the input provided by the user 103 may be "I have hand pain". Upon receiving the input, the system 107 detects the input. As an example, the input detected by the system 107 may be "I have head pain". Once, the input is detected, the system 107 extracts one or more voice parameters from pronunciation of the input. The one or more voice parameters may include, but not limited to, pitch range, word spacing [in terms of time gap between words], frequency, phonation threshold pressure, speed at which each word is uttered, time taken to utter the voice-based user input. Based on the one or more voice-parameters, the system 107 identifies a disease-type associated with the user 103. To identify the disease type associated with the user 103, the system 107 compares the one or more voice parameters with a second set of predetermined corresponding one or more voice parameters [alternatively referred as second set of voice parameters]. The second set of voice parameters are recorded for voice based user input uttered by one or more users affected by the one or more disease types and stored in the medical profile database 111. The medical profile database 111 may include medical profile of one or more users. As an example, the medical profile may include information such as disease type due to which voice parameters are affected, the second set of voice parameters and a first set of predetermined corresponding one or more voice parameters [alternatively referred as first set of voice parameters]. The first set of voice parameters is recorded for the input uttered by the one or more users when the one or more users are in normal condition.

Further, the system 107 verifies correctness of each word in the input based on comparison of each of the one or more voice parameters with the first set of voice parameters associated with the disease type. While verifying the correctness, each word in the input is compared with each word in the input uttered by one or more users during normal condition. At this stage, if the system 107 verifies that all the words in the input are detected correctly, then the system 107 may recommend the response for the input. However, the system 107 may detect one or more words incorrectly during the comparison. In such scenarios, the system 107 auto-corrects the one or more words which are detected incorrectly to form a corrected voice-based user input.

In an embodiment, the corrected voice-based user input is validated prior to recommending the response for the voice-based user input. The corrected voice-based user input is validated using a neural network technique. As an example, a Long Short Term Memory (LSTM) model may be used for validating the corrected voice-based user input. A person skilled in the art may note that any other technique not limited to LSTM model may be used for performing validation of the corrected voice-based user input. The system 107 recommends the response for the input upon validating the corrected voice-based user input.

Figure 2:
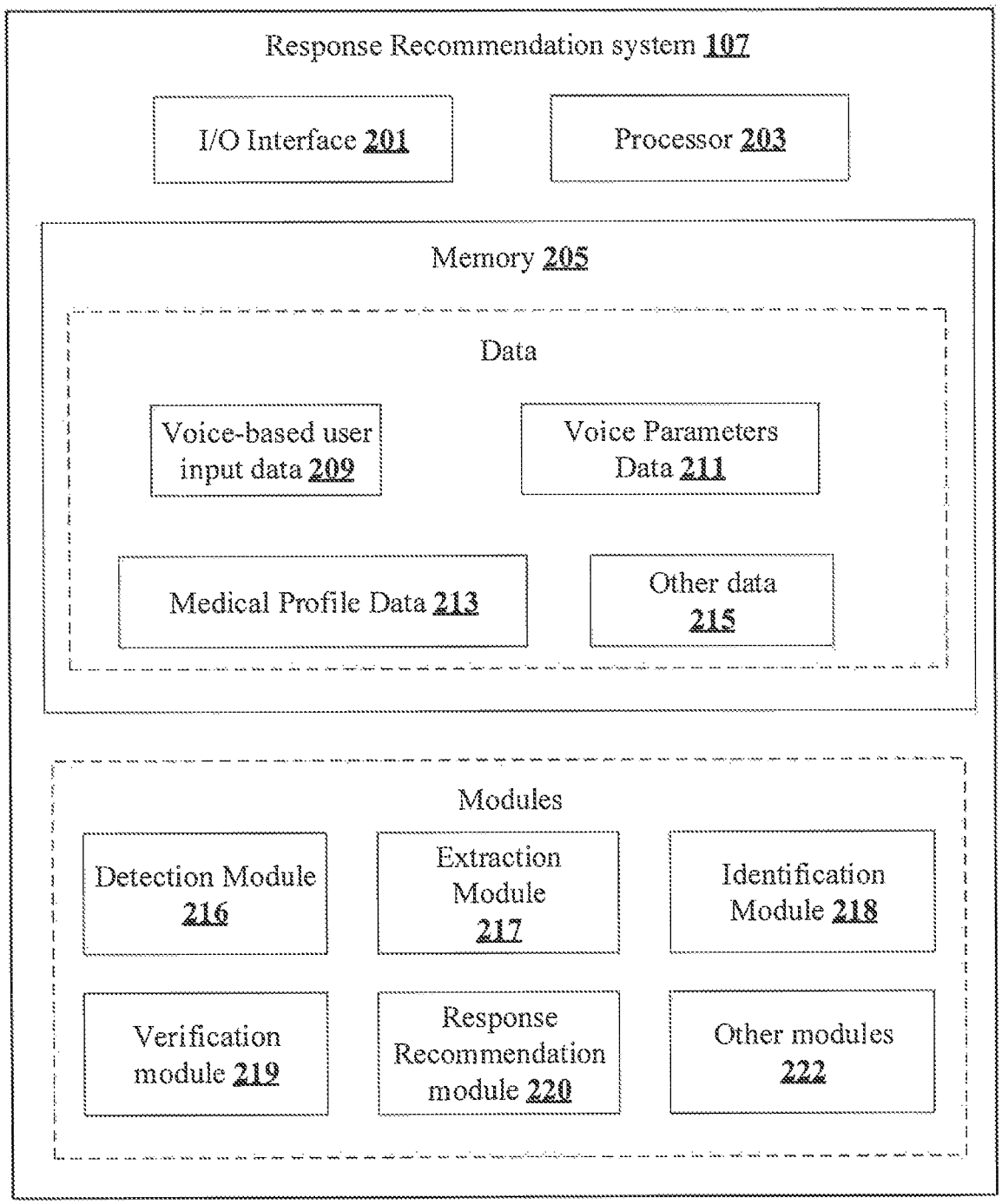
FIG. 2 shows a detailed block diagram illustrating a response recommendation system in accordance with some embodiments of the present disclosure.

FIG. 2 shows a detailed block diagram illustrating the response recommendation system 107 in accordance with some embodiments of the present disclosure.

The response recommendation system 107 may include an I/O interface 201, a processor 203, and a memory 205. The I/O interface 201 may be configured to receive the voice-based user input and to recommend a response for the input. The memory 205 may be communicatively coupled to the processor 203. The processor 203 may be configured to perform one or more functions of the response recommendation system 107.

In some implementations, the response recommendation system 107 may include data and modules for performing various operations in accordance with the embodiments of the present disclosure. In an embodiment, the data may be stored within the memory 205 and may include, without limiting to, voice-based user input data 209, voice parameters data 211, medical profile data 213 and other data 215.

In some embodiments, the data may be stored within the memory 205 in the form of various data structures. Additionally, the data may be organized using data models, such as relational or hierarchical data models. The other data 215 may store data, including temporary data and temporary files, generated by the modules for performing various functions of the response recommendation system 107.

In an embodiment, the voice-based user input data 209 may be received from the user 103 through the I/O interface 201 of the response recommendation system 107. The voice-based user input corresponds to a query provided by the user 103. In some embodiments, the user 103 may provide the voice-based user input to the response recommendation system 107 through an electronic device associated with the user 103. The electronic device may transmit the input to the response recommendation system 107. In an embodiment, the electronic device (not shown in figures) associated with the user 103 may include a smartphone, a Personal Assistance Device (PDA) or a computing device. In some embodiments, the electronic device may be configured to perform each functionality of the response recommendation system 107 without deviating from the scope of the present disclosure.

In an embodiment, the voice parameters data 211 may include data associated with one or more voice parameters extracted from pronunciation of the input. The one or more voice parameters may include at least one of pitch range, word spacing [in terms of time gap between words], frequency, speed at which each word is uttered, time taken to utter the voice-based user input and the like.

In an embodiment, the medical profile data 213 is retrieved from the medical profile database 111 associated with the response recommendation system 107. The medical profile data 213 includes information of medical profile of one or more users. The medical profile may include information such as a disease type due to which the voice parameters/characteristics are affected, first set of predetermined corresponding one or more voice parameters and second set of predetermined corresponding one or more voice parameters. The first set of predetermined corresponding one or more voice parameters are recorded for input uttered by one or more users when the one or more users are in normal condition. An average value of each of the first set of corresponding one or more voice parameters is calculated and stored in the medical profile database 111. The second set of predetermined corresponding one or more voice parameters are recorded for input uttered by one or more users when the one or more users are affected by the disease type. An average value of each of the second set of corresponding one or more voice parameters is calculated and stored in the medical profile database 111.

In an embodiment, one or more modules may process the data of the response recommendation system 107. In one implementation, the one or more modules may be stored as a part of the processor 203. In another implementation, the one or more modules may be communicatively coupled to the processor 203 for performing one or more functions of the response recommendation system 107. The modules may include, without limiting to, detection module 216, extraction module 217, identification module 218, verification module 219, response recommendation module 220 and other modules 222.

As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality. In an embodiment, the other modules 222 may be used to perform various miscellaneous functionalities of the response recommendation system 107. It will be appreciated that such modules may be represented as a single module or a combination of different modules. Furthermore, a person of ordinary skill in the art will appreciate that in an implementation, the one or more modules may be stored in the memory 205, without limiting the scope of the disclosure.

In an embodiment, the detection module 216 may be configured to detect the voice-based user input which corresponds to a query provided by the user 103. As an example, the user 103 may provide the query such as "I have hand pain, please suggest some physicians for consultation". The detection module 216 may detect the voice-based user input such as "I have head pain, please suggest some physicians for consultation".

In an embodiment, the extraction module 217 may be configured to extract one or more voice parameters from pronunciation of the voice-based user input. The one or more voice-parameters which are extracted may include, but not limited to, at least one of "pitch range". "word spacing [in terms of time gap between words]", "time taken to utter the voice-based user input", "phonation threshold pressure", "frequency" and the like. The person skilled in the art may note that any other voice-parameters may also be considered in the present disclosure.

As an example, the one or more voice-parameters which are extracted from pronunciation of the input "I have hand pain" but the detection module 216 detects it as "I have head pain" is as provided in the Table 1 below.

TABLE 1

| Pitch | Word spacing | Phonation threshold pressure | Time taken |
|---|---|---|---|
| >1.5 | >3 | 0.7 | >10 |

In an embodiment, the identification module 218 may be configured to identify disease type associated with the user 103 based on the one or more voice parameters. The identification module 218 compares the one or more'voice parameters with the second set of predetermined corresponding one or more voice parameters. The second set of predetermined corresponding one or more voice parameters correspond to one or more disease types. Based on the comparison, the identification module 218 may identify the disease type associated with the user 103.

In an embodiment, the verification module 219 may be configured to verify the correctness of each word in the voice-based user input based on comparison of each of the one or more voice parameters with a first set of predetermined corresponding one or more voice parameters associated with the disease type. Once the disease type is identified, the verification module 219 may compare the one or more voice parameters with the first set of predetermined corresponding one or more voice parameters associated with the disease-type. At this stage, each word in the voice-based user input is compared with each word in a voice-based user input uttered by one or more users during normal condition. As an example, the voice-based user 103 input uttered by one or more users during normal condition may be "I have hand pain". The voice-based user input detected by the system 107 may be "I have head pain".

The identification module 218 identifies one or more words which are detected incorrectly in the voice-based user input based on the comparison. The word "hand" is detected incorrectly as "head".

The response recommendation module 220 may be configured to auto-correct the one or more words which are detected incorrectly and to form a corrected voice-based user input. In the exemplary scenario, the word "head" which is detected incorrectly is replaced with the word "hand". Therefore, the corrected voice-based user input is "I have hand pain". Once the corrected input is formed, the response recommendation module 220 validates the corrected voice-based user input. If the corrected voice-based user input is validated, then the response recommendation module 220 provides the one or more responses for the corrected voice-based user input. The validation may be based on a neural network technique. As an example, LSTM model may be used for validating the corrected voice-based user input.

Henceforth, the process for recommending a response for a voice-based user input is explained with the help of one or more examples for better understanding of the present disclosure. However, the one or more examples should not be considered as limitation of the present disclosure.

Consider an exemplary scenario, wherein three users, user 1, user 2, and user 3 suffering from a disease type "Acute Laryngitis" and a medical profile database 111 is created. Due to the disease being suffered, the one or more voice parameters of these three users are affected. All the three users are made to utter a sentence related to symptom of the disease. In the case of "Acute Laryngitis", the users utter a sentence "I have hand pain" and the one or more voice parameters of the three users when the sentence is uttered is recorded and stored in the medical profile database 111. As an example, only three users are considered for creating the medical profile database 111. However, a person skilled in the art may note that any number of users who would be suffering with various disease types may be considered for training purpose and associated data may be stored in the medical profile database 111. The one or more voice parameters extracted from pronunciation of the sentence are "pitch range", word spacing [in terms of time gap between the words], time taken to utter the complete sentence, phonation threshold pressure and the like. The one or more voice parameters which are extracted are stored as second set of predetermined corresponding one or more voice-parameters.

The medical profile database 111 created for three users being suffered from the disease type "Acute Laryngitis" is as shown in the below Table 2.

TABLE 2

| | | Second Set of Predetermined corresponding one or more voice parameters | | | |
|---|---|---|---|---|---|
| User | Disease Type | Pitch | Word spacing [time gap] | Phonation threshold pressure | Time taken |
| User 1 | Acute Laryngitis | Pitch Range | | | |
| | | >2.0 | 3.1 | 0.8 | 10.5 |
| User 2 | Acute Laryngitis | Pitch | Word spacing | Phonation threshold pressure | Time taken |
| | | >1.5 | 4 | 0.9 | 15 |
| User 3 | Acute Laryngitis | Pitch | Word spacing | Phonation threshold pressure | Time taken |
| | | >1.6 | 3.5 | 1.2 | 12 |

The response recommendation system 107 calculates average of all the values for each of the second set of predetermined corresponding one or more voice parameters and the same is also stored in the medical profile database 111 as shown in the below Table 3.

TABLE 3

| | Second set of predetermined corresponding one or more voice parameters | | | |
|---|---|---|---|---|
| Disease Type | Pitch Range | Word spacing [time gap] | Phonation threshold pressure | Time taken |
| Acute Laryngitis | | | | |
| | 1.7 | 3.5 | 0.9 | 12.5 |

The average values stored in the medical profile database 111 corresponds to the disease type "Acute Laryngitis". In a similar manner, the second set of predetermined corresponding one or more voice parameters [which are average values of voice parameters of one or more users] are stored for one or more disease types as shown in below Table 4.

TABLE 4

| | Second set of predetermined corresponding one or more voice parameters | | | | First of predetermined corresponding one or more voice parameters | | | |
|---|---|---|---|---|---|---|---|---|
| Disease Type | Pitch Range | Word spacing [time gap] | Phonation threshold pressure | Time taken | Pitch Range | Word spacing [time gap] | Phonation threshold pressure | Time taken |
| Acute Laryngitis | >1.5 | >3 | >0.7 | >10 | 1 | 1 | 0.5 | 3 |
| Reflux Laryngitis | 1.0 | 3.0 | 0.5 | 9 | 1.2 | 1 | 1.0 | 4 |
| Vocal Chord paralysis | 1.2 | 3.2 | 0.5 | 9 | 1 | 1 | 0.5 | 3 |

Further, the three users are made to utter the sentence "I have hand pain" which is symptom of the disease type "Acute Laryngitis" when all the three users are in a normal condition. So, when the sentence is uttered, the one or more voice parameters are recorded and the same is also stored in the medical profile database 111 as a first set of predetermined corresponding one or more voice parameters. The average of all the values of each of the first set of predetermined corresponding one or more voice parameters of one or more users is calculated and the same is indicated in the Table 4 for one or more disease types.

As an example, user 103 namely, user 4 may provide the voice-based user input "I have hand pain" to the system 107. The system 107 may detect the input as "I have head pain". The system 107 extracts one or more voice parameters from pronunciation of the input. The one or more voice parameters which are extracted are as shown in the below Table 5.

TABLE 5

| | One or more voice parameters | | | |
|---|---|---|---|---|
| User User 4 | Pitch Range | Word spacing [time gap] | Phonation threshold pressure | Time taken |
| | 1.8 | 4 | 1.15 | 11.5 |

The one or more voice parameters are compared with the second set of predetermined corresponding one or more voice parameters as shown in Table 4 to identify the disease type. The values of one or more voice parameters in Table 5 matches with value of the second set of predetermined corresponding one or more voice parameters which corresponds to the disease type "Acute Laryngitis". Therefore, the system 107 identifies the disease type of the user 4 as "Acute Laryngitis". Once the disease type is identified, the system 107 obtains the first set of predetermined corresponding one or more voice parameters corresponding to the identified disease type. The first set of predetermined corresponding one or more voice parameters are recorded for the sentence "I have hand pain" uttered by the one or more users when the one or more users are in normal condition. The sentence uttered by the one or more users during normal condition i.e. "I have hand pain" is extracted by the system. At this stage, the system 107 compares each word in the input "I have head pain" which was detected by the system 107 with each word in the voice-based user input "I have hand pain" which is uttered by one or more users in a normal condition.

The voice-based user input detected by the system 107 is:

| I | Have | Head | Pain |
|---|---|---|---|

The voice-based user input uttered by one or more users during normal condition is:

| I | Have | Hand | Pain |
|---|---|---|---|

Based on the comparison, the system 107 detects that the word "hand" is detected incorrectly as "head". Therefore, the system 107 performs auto-correction of the word "head" and replaces the word "head" with "hand" and forms a corrected voice-based user input. The corrected voice based user input is "I have hand pain".

Further, the system 107 validates the corrected voice-based user input using a neural network model such as a LSTM model, in this scenario, the input to the LSTM model are, the voice based user input detected by the system 107 which is "I have head pain", the corrected voice-based user input which is "I have hand pain" and one or more previous voice-based user input. The one or more previous voice-based user input may be provided by the user 103 at the time of providing the query to the system 107 and the one or more previous voice-based user input may be stored in the medical profile database 111. In this scenario, there may be two previous voice-based user input such as:

Previous voice-based user input-1: I work in an automotive industry

Previous voice-based user input-2: Mostly, my work requires hands to be clean without any dust After extraction of the one or more previous voice-based user input, the LSTM model determines relationship among each word in the corrected voice-based user input with one or more previous voice-based user input for identifying a context of the user 103. Further, based on the determination, a knowledge graph is dynamically generated. The knowledge graph may include nodes and sub-nodes which are as shown below.

Main node: I have head pain
Sub-nodes 1: Automotive-head-pain-clean-work
Sub-nodes 2: Industry-head-pain-work-dust
Main node: I have hand pain
Sub-nodes 1: Automotive-hand-pain-clean-work
Sub-nodes 2: Industry-hand-pain-work-dust Out of the possible combinations, the node which matches the context of the user 103 is identified. In this scenario, since the user 103 is talking about keeping hands clean without any dust during work, the node which matches the context of the user 103 is "Automotive-hand-pain-clean-work". The identified node matches with the corrected voice-based user input and hence the corrected voice-based user input is validated.

In an embodiment, when the corrected voice-based user input is validated, the response recommendation system 107 may recommend the response for the corrected voice-based user input to the user 103. The recommended response may be list of physicians to consult for hand pain. The recommended response may also be in terms of recommending medications for the hand pain and the like.

Figure 3:
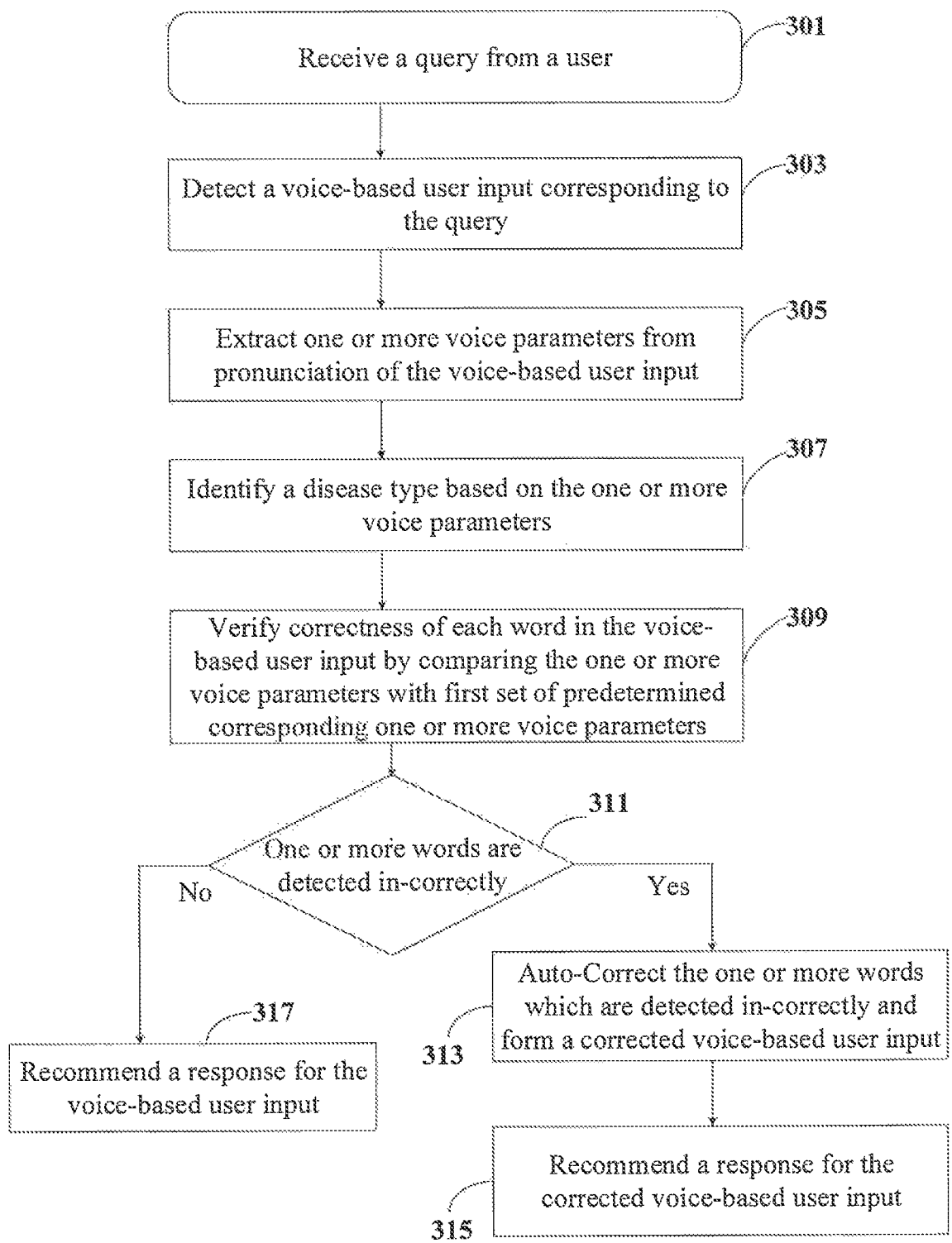
FIG. 3 shows a flowchart illustrating a method of recommending a response for a voice-based user input in accordance with some embodiments of the present disclosure.

FIG. 3 shows a flowchart illustrating a method of recommending a response for voice-based user input in accordance with some embodiments of the present disclosure.

As illustrated in FIG. 3, the method 300 includes one or more blocks illustrating a method for recommending a voice-based user input using a system 107, for example the response recommendation system 107 shown in FIG. 1. The method 300 may be described in the general context of computer executable instructions. Generally, computer executable instructions can include routines, programs, objects, components, data structures, procedures, modules, and functions, which perform specific functions or implement specific abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 301, the method includes, receiving, by a response recommendation system 107, a query from a user 103. The user 103 may provide a query such as "I have hand pain", please suggest some physicians for consultation". Upon receiving the query, the system 107 detects, at block 303, a voice-based user input which corresponds to the query.

At block 305, the method includes, extracting one or more voice parameters from pronunciation of the voice-based user input. The one or more parameters may include at least one of pitch range, word spacing, frequency, speed at which each word is uttered, and time taken to utter the voice-based user input and the like.

At block 307, the method includes, identifying a disease type associated with the user 103 based on the one or more voice parameters. To identify the disease type, the one or more voice parameters are compared with second set of predetermined corresponding one or more voice parameters. The second set of predetermined corresponding one or more voice parameters are recorded for voice-based user input uttered by one or more users affected by the one or more disease types. Based on the comparison, the disease type corresponding to the second set of predetermined corresponding one or more voice parameters, that matches the one or more voice parameters during the comparison is identified.

At block 309, the method includes verifying the correctness of each word in the voice-based user input based on comparison of each of the one or more voice parameters with a first set of predetermined corresponding one or more voice parameters which are associated with the disease type. At this stage, at block 311, each word in the voice-based user input is compared with each word in a voice-based user input uttered by one or more users during normal condition of the user 103. If all the words are detected correctly, then the method proceeds to block 317. If the one or more words are detected incorrectly then the method proceeds to block 313.

At block 317, the method includes recommending a response for the voice-based user input.

At block 313, the method includes, auto-correcting the one or more words which are detected incorrectly and forms a corrected input.

At block 315, the method includes recommending a response for the corrected voice-based user input.

Computer System

Figure 4:
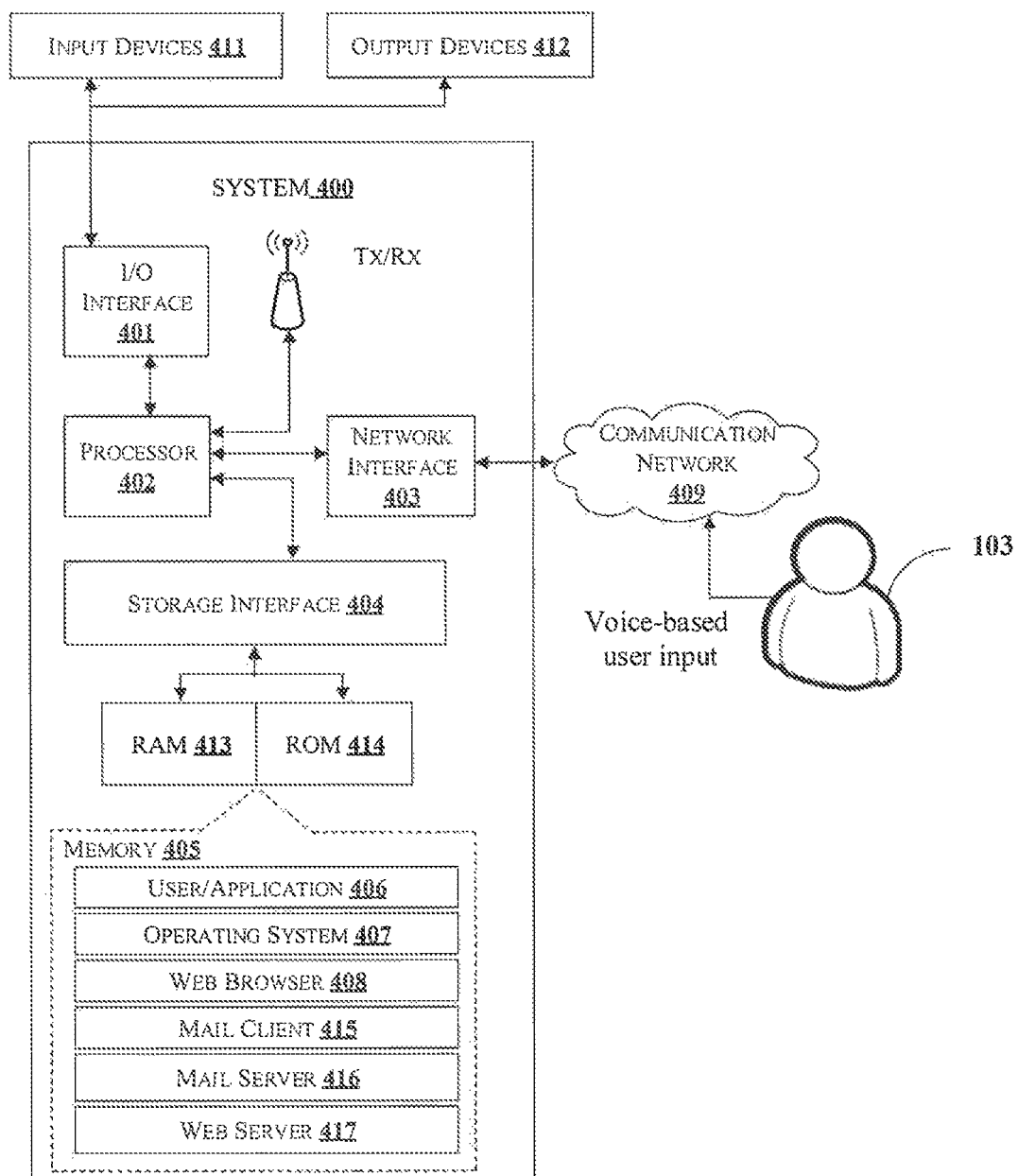
FIG. 4 illustrates a block diagram of an exemplary computer system for implementing embodiments consistent with the present disclosure.

FIG. 4 illustrates a block diagram of an exemplary computer system 400 for implementing embodiments consistent with the present disclosure. In an embodiment, the computer system 400 may be response recommendation system 107, which is used for recommending a response for a voice-based user input. The computer system 400 may include a central processing unit ("CPU" or "processor") 402. The processor 402 may comprise at least one data processor for executing program components for executing user 103 or system-generated business processes. A user 103 may include a person, a user 103 in the computing environment 100, a user 103 querying the response recommendation system 107, or such a device itself. The processor 402 may include specialized processing units such as integrated system (bus) controllers, memory management control units, floating point units, graphics processing units, digital signal processing units, etc.

The processor 402 may be disposed in communication with one or more input/output (I/O) devices (411 and 412) via I/O interface 401. The I/O interface 401 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE) or the like), etc. Using the I/O interface 401, the computer system 400 may communicate with one or more I/O devices 411 and 412. In some implementations, the I/O interface 401 may be used to connect to a user 103 device, such as a smartphone, a laptop, or a desktop computer associated with the user 103, through which the user 103 interacts with the response recommendation system 107.

In some embodiments, the processor 402 may be disposed in communication with a communication network 409 via a network interface 403. The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 403 and the communication network 409, the computer system 400 may communicate with the user 103 to receive the query and to provide the one or more responses.

The communication network 409 can be implemented as one of the several types of networks, such as intranet or Local Area Network (LAN) and such within the organization. The communication network 409 may either be a dedicated network or a shared network, which represents an association of several types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc.

In some embodiments, the processor 402 may be disposed in communication with a memory 405 (e.g., RAM 413, ROM 414, etc. as shown in FIG. 4) via a storage interface 404. The storage interface 404 may connect to memory 405 including, without limitation, memory drives, removable disc drives, etc., employing connection protocols such as Serial Advanced Technology Attachment (SATA), integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user 103/application 406, an operating system 407, a web browser 408, and the like. In some embodiments, computer system 400 may store user 103/application data 406, such as the data, variables, records, etc. as described in this invention. Such databases may be implemented as fault-tolerant, relational, scalable, secure databases such as Oracle or Sybase.

The operating system 407 may facilitate resource management and operation of the computer system 400. Examples of operating systems include, without limitation, Apple Macintosh OS X, UNIX, Unix-like system distributions (e.g., Berkeley Software Distribution (BSD), FreeBSD, Net BSD, Open BSD, etc.), Linux distributions (e.g., Red Hat, Ubuntu, K-Ubuntu, etc.), International Business Machines (IBM) OS/2, Microsoft Windows (XP, Vista/7/8, etc.), Apple iOS, Google Android, Blackberry Operating System (OS), or the like. A user 103 interface may facilitate display, execution, interaction, manipulation, or operation of program components through textual or graphical facilities. For example, user 103 interfaces may provide computer interaction interface elements on a display system operatively connected to the computer system 400, such as cursors, icons, check boxes, menus, windows, widgets, etc. Graphical User 103 Interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, JavaScript, AJAX, HTML, Adobe Flash, etc.), or the like.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Advantages of the Embodiment of the Present Disclosure are Illustrated Herein.

In an embodiment, the present disclosure discloses a method and system for recommending a response for a voice-based user input.

In an embodiment, the method of present disclosure detects one or more words in the voice-based user input which are detected incorrectly and auto-corrects the one or more words prior to recommending response for the voice-based user input.

In an embodiment, the method of present disclosure provides a better user experience as the user need not provide the same query repeatedly to receive correct responses.

In the present invention, the correction of the one or more words is performed by considering medical profile and state of the user and hence provides an accurate response recommendation.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise. The enumerated listing of items does not imply that any or all the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the invention.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Environment |
| 103 | User |
| 107 | Response recommendation system |
| 111 | Medical profile database |
| 201 | I/O interface |
| 203 | Processor |
| 205 | Memory |
| 209 | Voice-based user input data |
| 211 | Voice parameters data |
| 213 | Medical profile data |
| 215 | Other Data |
| 216 | Detection Module |
| 217 | Extraction module |
| 218 | Identification module |
| 219 | Verification module |
| 220 | Response recommendation module |
| 222 | Other modules |
| 400 | Exemplary computer system |
| 401 | I/O Interface of the exemplary computer system |
| 402 | Processor of the exemplary computer system |
| 403 | Network interface |
| 404 | Storage interface |
| 405 | Memory of the exemplary computer system |
| 406 | User/Application |
| 407 | Operating system |
| 408 | Web browser |
| 409 | Communication network |
| 411 | Input devices |
| 412 | Output devices |
| 413 | RAM |
| 414 | ROM |

The invention claimed is:

1. A method of recommending a response for a voice-based user input, the method comprising:

detecting, by a response recommendation system, the voice-based user input, wherein the voice-based user input corresponds to a query provided by a user;

extracting, by the response recommendation system, one or more voice parameters from pronunciation of the voice-based user input;

identifying, by the response recommendation system, a disease type associated with the user based on the one or more voice parameters, wherein identifying the disease type comprises:

comparing the one or more voice parameters with a second set of predetermined corresponding one or more voice parameters, wherein the second set of predetermined corresponding one or more voice parameters correspond to one or more disease types; and identifying the disease type among the one or more disease types, corresponding to the second set of predetermined corresponding one or more voice parameters, that matches the one or more voice parameters during the comparison;

verifying, by the response recommendation system, correctness of each word in the voice-based user input based on comparison of each of the one or more voice parameters with a first set of predetermined corresponding one or more voice parameters associated with the disease type; and recommending, by the response recommendation system, the response for the voice-based user input based on verification of the correctness of each word in the voice-based user input.

2. The method as claimed in claim 1, wherein the one or more voice parameters comprise at least one of a pitch, a word spacing, a frequency, a speed at which each word is uttered, and a time taken to utter the voice-based user input.

3. The method as claimed in claim 1, wherein the second set of predetermined corresponding one or more voice parameters are recorded for a voice-based user input uttered by one or more users affected by the one or more disease types.

4. The method as claimed in claim 1, wherein the first set of predetermined corresponding one or more voice parameters are recorded for a voice-based user input uttered by one or more users during normal condition.

5. The method as claimed in claim 4, wherein verifying the correctness of each word in the voice-based user input is performed by comparing each word in the voice-based user input with each word in the voice-based user input uttered by the one or more users during normal condition.

6. The method as claimed in claim 5 further comprising identifying one or more words detected incorrectly in the voice-based user input based on the comparison.

7. The method as claimed in claim 6 further comprising performing auto-correction of the one or more words detected incorrectly to form a corrected voice-based user input.

8. The method as claimed in claim 7 further comprising:

determining, by the response recommendation system, a relationship among each word in the corrected voice-based user input with one or more previous voice-based user input for identifying a context of the user, wherein the one or more previous voice-based user input is related to the query provided by the user;

generating, by the response recommendation system, a knowledge graph comprising one or more combination of nodes based on the voice-based user input, the corrected voice-based user input and each of the one or more previous voice-based user input;

identifying, by the response recommendation system, a node matching the context of the user; and validating, by the response recommendation system, the corrected voice-based user input when the identified node matches with the corrected voice-based user input.

9. The method as claimed in claim 1 comprises storing one or more medical profiles in a medical profile database associated with the response recommendation system, wherein each of the one or more medical profiles comprises information of a disease type being suffered by a user, a first set of predetermined corresponding one or more voice parameters and a second set of predetermined corresponding one or more voice parameters.

10. A response recommendation system for recommending a response for a voice-based user input, the response recommendation system comprising:

a processor; and a memory communicatively coupled to the processor, wherein the memory stores the processor-executable instructions, which, on execution, causes the processor to:

detect the voice-based user input, wherein the voice-based user input corresponds to a query provided by a user;

extract one or more voice parameters from pronunciation of the voice-based user input;

identify a disease type associated with the user based on the one or more voice parameters, wherein identifying the disease type comprises:

comparing the one or more voice parameters with a second set of predetermined corresponding one or more voice parameters, wherein the second set of predetermined corresponding one or more voice parameters correspond to one or more disease types; and identifying the disease type among the one or more disease types, corresponding to the second set of predetermined corresponding one or more voice parameters, that matches the one or more voice parameters during the comparison;

verify correctness of each word in the voice-based user input based on comparison of each of the one or more voice parameters with a first set of predetermined corresponding one or more voice parameters associated with the disease type; and recommend the response for the voice-based user input based on verification of the correctness of each word in the voice-based user input.

11. The response recommendation system as claimed in claim 10, wherein the one or more voice parameters comprise at least one of a pitch, a word spacing, a frequency, a speed at which each word is uttered, and a time taken to utter the voice-based user input.

12. The response recommendation system as claimed in claim 10, wherein the processor records the second set of predetermined corresponding one or more voice parameters for a voice-based user input uttered by one or more users affected by the one or more disease types.

13. The response recommendation system as claimed in claim 10, wherein the processor records the first set of predetermined corresponding one or more voice parameters for a voice-based user input uttered by one or more users during normal condition.

14. The response recommendation system as claimed in claim 13, wherein the processor verifies the correctness of each word in the voice-based user input by comparing each word in the voice-based user input with each word in the voice-based user input uttered by the one or more users during normal condition.

15. The response recommendation system as claimed in claim 14, wherein the processor is further configured to identify one or more words detected incorrectly in the voice-based user input based on the comparison.

16. The response recommendation system as claimed in claim 15, wherein the processor is further configured to perform auto-correction of the one or more words detected incorrectly to form a corrected voice-based user input.

17. The response recommendation system as claimed in claim 16, wherein the processor is further configured to:

determine a relationship among each word in the corrected voice-based user input with one or more previous voice-based user input for identifying a context of the user, wherein the one or more previous voice-based user input is related to the query provided by the user;

generate a knowledge graph comprising one or more combination of nodes based on the voice-based user input, the corrected voice-based user input and each of the one or more previous voice-based user input;

identify a node matching the context of the user; and validate the corrected voice-based user input when the identified node matches with the corrected voice-based user input.

18. The response recommendation system as claimed in claim 10, wherein the response recommendation system is associated with a medical profile database comprising one or more medical profiles, and wherein each of the one or more medical profiles comprises information of a disease type being suffered by a user, a first set of predetermined corresponding one or more voice parameters and a second set of predetermined corresponding one or more voice parameters.

* * * * *